United States Patent [19]
Baines et al.

[11] Patent Number: 6,165,510
[45] Date of Patent: Dec. 26, 2000

[54] INORGANIC MATERIAL IN PARTICLES FORM

[75] Inventors: Pamela Baines, Great Sankey; Peter William Stanier, Sandbach, both of United Kingdom

[73] Assignee: Crossfield Limited, Cheshire, United Kingdom

[21] Appl. No.: 09/117,979

[22] PCT Filed: Jan. 15, 1997

[86] PCT No.: PCT/EP97/00202

§ 371 Date: Aug. 11, 1998

§ 102(e) Date: Aug. 11, 1998

[87] PCT Pub. No.: WO97/30126

PCT Pub. Date: Aug. 21, 1997

[30] Foreign Application Priority Data

Feb. 12, 1996 [GB] United Kingdom .................... 9602797

[51] Int. Cl.⁷ ...................................................... A61K 9/14
[52] U.S. Cl. ........................................... 424/489; 424/401
[58] Field of Search ..................................... 424/489, 464, 424/270, 78.03, 401

[56] References Cited

U.S. PATENT DOCUMENTS 4,265,899  5/1981  Lewis et al. ............................ 424/270

FOREIGN PATENT DOCUMENTS 2 303 763   10/1976   France .
195 31 044   2/1996   Germany .
94 12151     6/1994   WIPO .
96 30304    10/1996   WIPO .

OTHER PUBLICATIONS

Patent abstracts of Japan vol. 15, No. 293 (C–853), Jul. 25, 1991 and JP 03 106984 (Mitsubishi Kasei Corp.) May 7, 1991.

*Primary Examiner*—Thurman K. Page
*Assistant Examiner*—William E. Benston, Jr.
*Attorney, Agent, or Firm*—Pillsbury Madison & Sutro LLP

[57] ABSTRACT

A cosmetic composition includes an inorganic material in granular form which, under condition of use of the cosmetic composition, breaks down to a particle size wherein less than 5% by weight, preferably less than 2% by weight, most preferably less than 1% by weight is above 45 microns, as measured by wet sieve analysis.

24 Claims, No Drawings

INORGANIC MATERIAL IN PARTICLES FORM

This Appln. is a 371 of PCT/EP97/00202 filed Jan. 15, 1997.

FIELD OF THE INVENTION

The present invention relates to an inorganic material in particles form useful in cosmetic compositions. The present invention most specifically relates to an exfoliating and/or massaging and/or cleansing material. The present invention also relates to a cosmetic composition containing said inorganic material.

BACKGROUND OF THE INVENTION

Exfoliation and cleansing of the skin is an essential element of body care. Exfoliating compositions are well known in the art. Such compositions may, by abrasion, remove residual make-up and dead cells from the surface of the skin in order to prevent pores clogging. This is achieved by abrasive particles suspended in said compositions.

In the past, two particulate abrasive materials were used; calcium carbonate and the endocarp of apricot seeds. It was recently recognized that these abrasive materials had an inherent grittiness and that it was desirable to produce an abrasive material which has an initial skin feel which would disappear while using the cosmetic formulation.

Thus, it has been disclosed in EP-A-670,712 an exfoliating composition including a particulate exfoliating material with a particle size in the range of 0.03 to 3mm, wherein the particulate material comprises an agglomerated silica having a primary particle size in the range of 0.01–0.2 microns, which is friable and under conditions of use of the composition break up into particles having an average size of less than 40 microns.

Only one type of silica agglomerate is disclosed in this document and it is described as an agglomerate of Sident 22S.

It is disclosed in this document that the inherent grittiness of the suspended abrasive particles is avoided. It is further disclosed that particles with average size of less than 40 microns do not feel gritty and that the average particle size, after break up of the exfoliating particles, will be less than 40 μm.

Nevertheless, it has been found that, whilst the grittiness is reduced, the particles are still felt by the user as a residue on the skin.

A desirable feature following particle breakdown would be the perception by the user of a creamy smooth lather of the product on the skin and gentle cleansing. It has been found that the use of silica agglomerates as described in EP-A-670,712 did not give this effect because they do not fully breakdown and therefore do not contribute, by way of a thickening effect that smaller particles can provide, to the resultant lather.

There is therefore a need for exfoliating particles which, whilst providing the required exfoliating performance, progressively break down to a point at which they are no longer detected. It is also desirable for such exfoliating particles to give a creamy, smooth lather on breakdown in a cosmetic composition.

Tests and Definitions i) Oil Absorption

The oil absorption is determined by the ASTM spatula rub-out method (American Society Of Test Material Standards D, 281).

The test is based on the principle of mixing linseed oil with the silica by rubbing with a spatula on a smooth surface until a stiff putty-like paste is formed which will not break or separate when it is cut with a spatula. The volume of oil used is then put into the following equation:

$$\text{Oil absorption} = \frac{\text{cm}^3 \text{ oil absorption} \times 100}{\text{Wt. of silica sample in g}}$$

$$= \text{cm}^3 \text{ oil}/100 \text{ g silica}$$

ii) Weight Mean Particle Size

The weight mean particle size of the water insoluble particulate before agglomeration is determined using a Malvern Mastersizer model X, made by Malvern Instruments, Malvern, Worcestershire with MS15 sample presentation unit. This instrument uses the principle of Fraunhoffer diffraction, utilising a low power He/Ne laser. The water insoluble particulates are dispersed ultrasonically in water for 7 minutes to form an aqueous suspension and then mechanically stirred before they are subjected to the measurement procedure outlined in the instruction manual for the instrument, utilising a 45 mm lens in the detector system.

The Malvern Particle Sizer measures the weight particle size of the water insoluble particulate. The weight mean particle size ($d_{50}$) or 50 percentile, the 10 percentile ($d_{10}$) and the 90 percentile ($d_{90}$) are easily obtained from the data generated by the instrument.

iii) Granular Strength

EP-A-670712 describes a test to measure agglomerate strength in dry powder conditions. It is considered that this test is not representative of the conditions which prevail when a cosmetic composition is used and the granules are breaking down in an aqueous system.

It was therefore necessary to develop a more representative test, which is carried out in the presence of water and subjects the granule to controlled de-aggregation.

Granule breakdown characterisation was carried out using a Microson XL2020 Sonicator programmable ultrasonic liquid processor, manufactured by Misonix Inc. Farmingdale, N.Y. and supplied in the UK by Labcaire Systems Ltd, Avon.

The Microson XL2020 Sonicator ultrasonic processor has a maximum of 550 watts output with a 20 KHz convertor and is fitted with a ¾ inch tapped horn. The processor has variable amplitude control and a microprocessor controlled digital timer integrated with a Pulsar cycle timer with power output and elapsed time displays.

The piezoelectric convertor transforms electrical energy to mechanical energy at a frequency of 20 KHz. Oscillation of piezoelectric crystals is transmitted and focused by a titanium disrupter horn that radiates energy into the liquid being treated. A phenomenon known as cavitation, the formation and collapse of microscopic vapour bubbles generated by the strong sound waves produces a shearing and tearing action. Almost all of the activity takes place just in front of the probe tip.

The generator provides high voltage pulses of energy at 20 KHz and adjusts for varying load conditions, such as viscosity and temperature. It senses impedence change and increases or decreases power to the probe tip automatically.

The ¾ inch probe is a medium intensity horn for processing volumes between 25 and 500 ml. The maximum amplitude at the tip of the probe is 60 microns. Hence, sonicator processors operating at output control setting 10 have 60 microns of amplitude (peak to peak amplitude of the radiating face of the tip) at the tip of the probe.

Therefore, there is a linear relationship between the output control knob (or amplitude adjustment knob) and the amplitude at the tip of the probe., ie 6 micons of amplitude per control knob setting. The generator draws energy accordingly to maintain a constant amplitude at the tip for a given output control setting. This is displayed on the % output power meter and is energy in Watts (ie output=%/100*550 watts available=x watts delivered)

A paper given by Mr S Berliner, (Director, Technical Services, Heat Systems-Ultrasonics Inc.) at the 9th Annual Technical Symposium of the Ultrasonic Industry Association, entitled "Application of Ultrasonic Processors (Power vs Intensity in Sonification)" provides further detailed information of the principles involved in this experimental technique.

Procedure:

A 250 ml pyrex beaker is insulated and fitted with a lid with a ¾ inch hole in the centre to accommodate the ultrasonic probe and a ⅛ inch hole to the side to accommodate a temperature probe.

Into the insulated beaker weigh the desired amount of deionised water, maintained at a constant temperature of 21° C. and the desired amount of inorganic granule to obtain a final weight of 200 g. A magnetic stirrer bar is introduced into the beaker and the beaker is placed on a magnetic stirrer hotplate equipped with a temperature sensor (Heidolph MR3003 magnetic stirrer hotplate with a stainless steel PT-100 temperature sensor and rpm stirrer speed, obtainable from Orme Scientific, Manchester. The beaker contents are stirred on setting 3 (~300 rpm), the ultrasonic probe is immersed to a depth of ⅝ inch into the liquid and the temperature sensor is inserted into the liquid to continuously monitor temperature.

The Sonicator ultrasonic processor is switched on and information on processing time and pulsed mode programmed, as required.

Cavitation is introduced to the system by turning the output control knob to the desired amplitude setting, whilst the temperature profile is closely monitored. The % power output required to maintain the amplitude at the tip is also recorded, according to the setting.

When the cavitation process is complete, the stirrer is switched off and the magnetic stirrer bar is removed. Manual stirring is continued with a spatula to maintain dispersion.

+45 micron Wet Sieve Test Method

The inorganic particle dispersion is poured through a 45 micron sieve. Any residue in the beaker is washed through the sieve, using half the amount of initial water. The sieve is then dried to constant weight in an oven at 105° C. The residue which remains on top of the 45 micron sieve is then weighed and expressed as a percentage of the initial weight of inorganic granule. The greater the amount retained on the sieve, the stronger the agglomerate strength of the granule and the more difficult it is to breakdown. An optimum product will have no residue remaining on the sieve.

It has been found that, for a granule to satisfactorily breakdown in cosmetic compositions, it will have less than 5%, preferably less than 2%, most preferably less than 1% by weight, residue on a +45 micron sieve after ultrasonification on setting 10 (60 micron amplitude) for a period of 7 minutes.

iv) Particle Size Distribution by Sieve Analysis

An accurate measure of the true particle size distribution of the granular composition is done using sieve analysis.

100 g of the sample is placed on the top sieve of a series of BS sieves, at approximately 50 micron intervals to cover the particle size range of the granule. The sieves are arranged in order with the finest at the bottom and the coarsest at the top of the stack. The sieves are placed in a mechanical vibrator eg Inclyno Mechanical Sieve Shaker by Pascall Engineering Co. Ltd., covered with a lid and shaken for 10 minutes. Each sieve fraction is accurately weighed and the results calculated:

$$\% \text{ residue} = \frac{\text{Wt. of residue} * 100}{\text{Wt. of sample}}$$

v) BET Surface Area

Surface area is determined using standard nitrogen adsorption methods of Brunauer, Emmett and Teller (BET), using a single point method with a Sorpty 1750 apparatus supplied by Carlo Erba company of Italy. The sample was outgassed under vacuum at 270° C. for 1 hour before measurement.

GENERAL DESCRIPTION OF THE INVENTION

It is a first object of the present invention to provide an inorganic material in granular form having a granular strength such that less than 5%, preferably less than 2%, most preferably less than 1% by weight, residue remains on a 45 micron wet sieve after ultrasonification for 7 minutes with 60 micron amplitude of vibration.

Preferably, the inorganic material comprises at least 95% by weight of amorphous silicas.

More preferably, the inorganic material comprises at least 95% by weight of amorphous silica agglomerates.

Even more preferably the inorganic material in granular form comprises at least 95% w/w of a water insoluble particulate, whereby 5 to 90% of the water insoluble particulate is made from a water insoluble particulate material, having a weight mean particle size of less than 20 microns and an oil absorption capacity of 90 to 145 $cm^3/100$ g, and selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice, and 5 to 90% of the water insoluble particulate is made from an amorphous silica, having a weight mean particle size of below 20 microns and an oil absorption 150 to 190 $cm^3/100$ g.

Also more preferably the inorganic material in granular form comprises at least 95% w/w of a water insoluble particulate, whereby 5 to 90% of the water insoluble particulate is made from a water insoluble particulate material, having a weight mean particle size of less than 20 microns and an oil absorption capacity of 90 to 145 $cm^3/100$ g, and selected from the group consisting of aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice, and 5 to 90% of the water insoluble particulate is made from an amorphous silica, having a weight mean particle size of below 20 microns and an oil absorption 130 to 190 $cm^3/100$ g.

Preferably, the inorganic material has a particle size of 95% below 1000 microns and 95% above 45 microns, as measured by sieve analysis.

The inorganic material in granular form can be produced by any agglomeration or compaction technique.

Agglomeration can be achieved for example by pan granulation, dry roller compaction, extrusion, spray granulation or spinning disc granulation.

When the agglomeration is performed in a pan granulator, the water:solids ratio for products of this invention is preferably in the range 1.0:1 to 1.25:1. This ratio is important to achieve agglomerates of correct strength, since below this the material remains a powder and above this a paste is formed. Using this method the agglomerates need to be dried. This drying can be done in several ways, eg in an oven or in a fluidised bed. During this drying stage, the required degree of strength is built into the agglomerates.

Once compacted, the agglomerates are then reduced in size according to the desired particle size range in the product application.

Owing to the porous nature of the agglomerates, it is possible for them to act as delivery vehicles for substances that give cosmetic benefits such as colouring pigments, flavours, perfumes or other cosmetic ingredient. Such substances may be contained within the pores of the material.

If coloured granules are required, then suitable coloured pigments, for example pigment dispersions under the Cosmenyl trade name or pigment powders under the Hostaperm trade name or Cosmetic Pink RC 01 (D & C Red No 30) supplied by Hoechst or Ultramarine Grade 54 supplied by Holliday Pigments, can be added to the composition of the granule, without affecting the strength of the granule.

It is a second object of the present invention to provide a cosmetic composition comprising such inorganic material in granular form.

When a cosmetic composition is used, for example by hand massage on the skin, the shear and crush forces which are created cause the particles of inorganic material in granular form to break up after a short period of time, typically from 10 to 25 seconds, preferably less than 20 seconds, to such an extent that they can no longer be felt.

It is a third object of the present invention to provide a cosmetic composition including an inorganic material in granular form, characterised in that the inorganic material in granular form, under condition of use of the cosmetic composition, breaks down to a particle size wherein less than 5% by weight, preferably less than 2% by weight, most preferably less than 1% by weight is above 45 microns, as measured by wet sieve analysis.

Preferably, the cosmetic composition is in the form of a liquid, an emulsion or a multiple emulsion. By suitable adjustment of the solid to liquid ratio, and the viscosity of the liquid phase, the composition may take any physical form from a thick paste or gel to a low viscosity liquid.

In the cosmetic compositions of the present invention, the level of inorganic material in granular form may be from 1 to 20% by weight, preferably 1 to 10%, more preferably 3 to 10% by weight, even more preferably 3 to 5%.

The cosmetic composition of the invention may contain one or more additional components depending on the end use of the product, typical end uses being personal wash off products for example shower gels, facial cleansers and shampoos.

Cleaning compositions also comprise one or more surfactants, preferably selected from anionic, nonionic, amphoteric and zwitterionic surfactants and mixtures thereof. The surfactants may be present in a total amount of from 1% to 50% by weight, preferably from about 2% to 30% by weight.

Water is another component of the cosmetic compositions of the present invention and may be present in an amount from 10% to 90% by weight, preferably from 20% to 80% by weight, more preferably from 40% to 75% by weight.

In cosmetic compositions of the present invention it is preferred that one or more thickening or suspending agents are included in order that the inorganic material in granular form remains stably dispersed throughout the composition. These agents may be present in the compositions in a total amount of from 0.1 to 60% by weight depending on the nature of the agents.

The cosmetic compositions of the invention may also contain other components conventionally found in cosmetic compositions for hair or skin.

Compositions in accordance with the present invention may be made by conventional methods of preparing cosmetic compositions, eg facial scrubs. If suspension is through surfactant lamellar phase formation, however, it is preferable that the particulate material is incorporated in the composition prior to the formation of the lamellar phase which stabilises the dispersed particles, in order for the particulate material to be successfully and stably incorporated therein. Alternatively, for creams and pastes, the base composition may be prepared by mixing the base ingredients, with addition of thickener or suspending agent if used, followed by low shear mixing of the pre-prepared particulate material.

It is important that in the preparation of compositions in accordance to the present invention and any mixing be done at sufficiently low shear that the inorganic material in granular form does not experience forces sufficiently great to cause the particles to fracture.

DETAILED DESCRIPTION OF THE INVENTION

The present invention will be further described in the following examples.

COMPARATIVE EXAMPLE 1

A silica granule was prepared according to EP-A-670,712. A single silica of high structure, Sorbosil TC15 (obtainable from Joseph Crosfield and Son—England) was agglomerated at 200 g powder batch size, laboratory scale with deionised water (water:solids ratio of 2.1:1) using a Sirman Sv6 mixer, supplied by Metcalfe Catering Equipment Ltd, Blaenau Ffestiniog, Wales.

The resulting wet agglomerate was then dried in an oven at 150° C. for 4 hours, gently forced through a 500 micron screen and sieved at 106 microns to adjust the particle size distribution.

The silica has the following properties:

| Sorbosil TC15* | | |
|---|---|---|
| Oil Absorption (cm$^3$/100 g) | | 339 |
| Weight mean Particle Size: | D10 | 5.6 |
| (microns) | D50 | 12.9 |
| | D90 | 29.3 |
| Surface Area (m$^2$g$^{-1}$) | | 260 |

\* - Obtainable from Crosfield Ltd, England.

In order to determine the granule composition strength and breakdown characterisation, the agglomerated silica granule was subjected to ultrasonification using a Microson XL2020 Sonicator as described in part iii) of tests and definitions.

The weight of granule used in the test was 1 g and deionised water was added to achieve a final weight of 200 g. The ultrasonic processor was programmed for timed and pulsed mode to achieve maximum amplitude at the tip for a period of 7 minutes. The processor was programmed to pulse on for 30 seconds and pulse off for 20 seconds to achieve a total process time of 7 minutes with minimum heat increase. The output control knob was turned to setting 10 to achieve a maximum amplitude of 60 microns at the tip and the programme started. The temperature of the dispersion was continuously monitored and was found to rise to 42° C.

When cavitation was complete the inorganic particle dispersion was poured through a 45 micron sieve and dried to constant weight as described in part iii) of tests and definitions.

In order to determine the wet sieve residue retained at 45 microns with no ultrasonification the same weight of agglomerate:water was used as described above. The inorganic particle dispersion was stirred to maintain dispersion with a spatula and poured straight through a 45 micron sieve, washed through with 100 cm$^3$ of de-ionised water and dried to constant weight as described in part iii) of tests and definitions.

COMPARATIVE EXAMPLE 2

Two silicas one of high structure, Sorbosil TC15 and medium, bordering upon low structure, Sorbosil AC77 (obtainable from Crosfield Ltd, England.) were blended together in 1:1 ratio by weight and agglomerated at 200 g powder batch size, laboratory scale with de-ionised water (water: solids ratio of 1.33:1) using a Sirman SV6 mixer, supplied by Metcalfe Catering Equipment Ltd, Blaenau Ffestiniog, Wales.

The resulting wet agglomerate was then dried in an oven at 150° C. for 4 hours, gently forced through a 500 micron screen and sieved at 106 microns to adjust the particle size distribution.

Sorbosil AC77 has the following properties:

| Sorbosil AC77* | | |
|---|---|---|
| Oil Absorption (cm$^3$/100 g) | | 129 |
| Weight mean particle size: | D 10 | 2.7 |
| (microns) | D 50 | 8.1 |
| | D 90 | 17.8 |
| Surface Area (m$^2$g$^{-1}$) | | 120 |

The granule composition strength and breakdown characterisation of the agglomerated silica was carried out as described in Example 1.

EXAMPLE 3 OF THE INVENTION

Two silicas, one of medium bordering upon low structure, Sorbosil AC39* and medium structure Neosyl AC* were blended together in a 3:1 ratio by weight. The resulting silica blend was agglomerated at 200 g powder batch size, laboratory scale with deionised water (water: solids ratio of 1.1:1) using a Sirman SV6 mixer, supplied by Metcalfe Catering Equipment Ltd, Blaenau Ffestiniog, Wales.

*—Obtainable from Crosfield Ltd, England.

The resulting wet agglomerate was then dried in an oven at 150° C. for 4 hours, gently forced through a 500 micron screen and sieved at 106 microns to adjust the particle size distribution.

The silicas have the following properties:

| PROPERTY | | Sorbosil AC39(*) | Neosyl AC(*) |
|---|---|---|---|
| OIL ABSORPTION (g/100 g) | | 125 | 155 |
| WEIGHT MEAN | $D_{10}$ | 3.2 | 3.7 |
| PARTICLE SIZE | $D_{50}$ | 11.3 | 11.9 |
| (microns) | $D_{90}$ | 31.7 | 38.1 |

* - Obtainable from Crosfield Ltd, England.

The granule composition strength and breakdown characterisation of the agglomerated silica was carried out as described in Example 1.

EXAMPLE 4 OF THE INVENTION

Two silicas, one of medium structure, Neosyl AC* and medium, bordering upon low structure, Sorbosil AC35* were blended together in a 9:1 ratio by weight. The resulting silica blend was agglomerated at 200 g powder batch size, laboratory scale with deionised water (water: solids ratio of 1.25:1) using a Sirman SV6 mixer, supplied by Metcalfe Catering Equipment Ltd, Blaenau Ffestiniog, Wales.

*—Obtainable from Crosfield Ltd, England.

The resulting wet agglomerate was then dried in an oven at 150° C. for 4 hours, gently forced through a 500 micron screen and sieved at 106 microns to adjust the particle size distribution.

ISorbosil AC35 has the following properties:

| Sorbosil AC35* | | |
|---|---|---|
| Oil Absorption (cm$^3$/100 g) | | 100 |
| Weight mean particle size: | D10 | 1.6 |
| (microns) | D50 | 10.0 |
| | D90 | 29.7 |

EXAMPLE 5 OF THE INVENTION

Two silicas, one of medium bordering upon low structure, Sorbosil AC39* and medium structure Neosyl AC* were blended together in a 9:1 ratio by weight. The resulting silica blend was agglomerated at 200 g powder batch size, laboratory scale with deionised water (water: solids ratio of 1.1:1) using a Sirman SV6 mixer, supplied by Metcalfe Catering Equipment Ltd, Blaenau Ffestiniog, Wales.

*—Obtainable from Joseph Crosfield & Sons, England.

The resulting wet agglomerate was then dried in an oven at 150° C. for 4 hours, gently forced through a 500 micron screen and sieved at 106 microns to adjust the particle size distribution.

EXAMPLE 6 OF THE INVENTION

A coloured agglomerate was prepared with the same silica composition blend as example 3, to 97% with 3% Ultramarine Blue Grade 54* incorporated in the silica blend. The same processing, drying and particle size adjustments were followed as described in example 3.

* Supplied by Holliday Pigments, Humberside, England

Results:

Below are the results of the % agglomerate residue retained on the 45 micron sieve.

| Agglomerate I.D. | No Ultrasonification | 60 microns of amplitude for 7 mins. |
| --- | --- | --- |
| EX 1 | 95 | 57 |
| EX 2 | 91 | 40 |
| EX 3 | 79 | 0 |
| EX 4 | 88 | 1 |
| EX 5 | 90 | 0 |
| EX 6 | 95 | 0 |

It can be seen that prior art silica granule made according to WO 94/12151 is too strong and does not breakdown to particles which cannot be felt on the skin. Similarly, a weaker granule in which half of the high structured Sorbosil TC15 silica is replaced with a much lower structured silica, Sorbosil AC77, is still much too strong for this type of application, where an optimum product such as examples 3 to 6 fully break down and can no longer be felt on the skin.

EXAMPLE 7 (Facial Scrub)

The following oil-in-water (O/W) emulsion was prepared in which inorganic materials according to examples 1 to 4 were used.

| Component | % wt |
| --- | --- |
| Phase A | |
| Inorganic material | 5.00 |
| Mineral oil | 20.00 |
| Primary alcohols, mixture[1] | 10.00 |
| Glyceryl Stearate SE | 4.00 |
| Ceteareth-12 | 1.50 |
| Ceteareth-20 | 1.50 |
| Glyceryl monooleate | 1.00 |
| Propylparaben | 0.05 |
| Phase B | |
| Deionised water | to 100% |
| Methylparaben | 0.10 |
| Phase C | |
| Fragrance | qs |

[1]Acropol 35 ( ex Exxon Chemicals France )

Procedure
1. Add the ingredients of Phase A in the order shown and stir at 1000 rpm. Heat to 70° C.
2. Heat Phase B to 75° C. When at temperature add Phase B to Phase A with stirring maintained at 1000 rpm. When homogenous cool to 40° C.
3. Add Phase C and mix thoroughly at low stirrer speed.

When used by trained panellists, it was found that Examples 1 and 2 lead to harsh initial skin feeling and particles left a gritty residue after 2 minutes rubbing on the skin (by rubbing between the palms of the hands). No lathery effect was perceived. This technique of rubbing between the palms of the hands was used in subsequent examples 8 to 10 to evaluate agglomerate breakdown on the skin.

Example 4 lead to a good initial skin feel where the particles were perceived and broke down in 25 seconds. A creamy smooth lather resulted.

Example 3 lead to good initial skin feel where the particles were perceived and broke down in 17 seconds. A creamy smooth lather resulted leaving a fresh clean feel.

EXAMPLE 8 (Shower gel)

The following shower gel composition was produced using the agglomerate according to example 3 as the inorganic material.

| Component | % wt |
| --- | --- |
| Sodium lauryl ether sulphate[2] ( 27% ) | 12.00 |
| Cocamidopropyl betaine[3] ( 30% ) | 2.00 |
| Coconut Diethanolamide[4] | 1.00 |
| Inorganic material | 5.00 |
| Sodium chloride | 10.00 |
| Perfume, colouring, preservatives | qs |
| Deionised water | to 100% |

[2]Empicol ESB3/M ( ex. Albright & Wilson )
[3]Empigen BS/P ( ex. Albright & Wilson )
[4]Empilan CDE ( ex. Albright & Wilson )

Procedure:
1. Dissolve salt or other lamellar phase-forming component in water, without heating.
2. Add preservative
3. Add particulate material with mixing.
4. Add sodium lauryl ether sulphate.
5. Add any other optional ingredients, eg opacifier, pearlescer, colourant, perfume, etc.
6. Finally add cocamidopropyl betaine and coconut diethanolamide.

The shower gel with agglomerate according to example 3 lead to good initial skin feel where the particles were perceived and broke down in 17 seconds. A creamy smooth lather resulted leaving a fresh clean feel.

EXAMPLE 9 (Shower gel)

The following shower gel composition was produced using the agglomerate according to example 5 as the inorganic material.

| Component | % wt |
| --- | --- |
| Sodium lauryl ether sulphate[2] ( 70% ) | 12.00 |
| Cocamidopropyl betaine[3] ( 30% ) | 2.00 |
| Coconut Diethanolamide[4] | 1.00 |
| Inorganic material | 5.00 |
| Amorphous silica[5] | 3.00 |
| Sodium chloride | 5.00 |
| Perfume, colouring, preservatives | qs |
| Deionised water | to 100% |

[2]Elfan NS 243S ( ex. Akzo )
[3]Empigen BS/P ( ex. Albright & Wilson )
[4]Empilan CDE ( ex. Albright & Wilson )
[5]Amorphous silica thickener according to U.S. Pat. No. WO94/11302 with the particle size distribution adjusted to $D_{10}$ 1.1 um, $D_{50}$ 4.4 um and $D_{90}$ 9.2 um obtainable from Joseph Crosfield & Sons, England.

Procedure:
1. Dissolve salt or other lamellar phase-forming component in water and heat to ~70° C.
2. Disperse silica thickener thoroughly.
3. Add preservative
4. Add particulate material with mixing.
5. Add sodium lauryl ether sulphate.
6. Cool to ~50° C. and add any other optional ingredients, eg opacifier, peariescer, colourant, perfume, etc.
7. Finally add cocamidopropyl betaine and coconut diethanolamide and cool to room temperature The shower gel with agglomerate according to example 5 lead to good initial skin feel where the particles were perceived and broke down in 12 seconds. A creamy smooth lather resulted leaving a fresh clean feel.

EXAMPLE 10 (Clear facial gel)

The following facial gel composition was produced using the agglomerate according to example 6 as the inorganic material.

| Component | % wt |
| --- | --- |
| Ammonium lauryl sulphate[6] ( 30% ) | 50.00 |
| Cocamidopropylbetaine ( 30% ) | 15.00 |
| Carbomer[7] | 1.55 |
| Inorganic material ( as per example 6 ) | 1.00 |
| Perfume, preservatives | qs |
| Water | to 100% |

[6]Empicol AL30/T ( ex. Albright & Wilson )
[7]Carbopol Ultrez 10 ( ex. B.F. Goodrich )

Procedure:
1. Disperse carbomer thoroughly in water and increase temperature to ~50° C. and mix for 20 mins.
2. Switch off heat and add preservatives and perfume.
3. Add surfactants and mix thoroughly.
4. Finally cool to room temperature and stir in inorganic material.

The clear facial gel with agglomerate according to example 6 lead to good initial skin feel where the coloured visible particles in a clear base were perceived and broke down in 20 seconds. A creamy smooth lather resulted leaving a fresh clean feel.

What is claimed is:

1. Inorganic material in granular form having a granular strength such that less than 5% by weight residue remains on a 45 micron wet sieve after ultrasonification for 7 minutes with 60 micron amplitude of vibration.

2. Inorganic material according to claim 1 comprising at least 95% by weight of amorphous silicas.

3. Inorganic material according to claim 2 comprising at least 95% by weight of amorphous silica agglomerates.

4. Inorganic material in granular form according to claim 1, comprising at least 95% w/w of a water insoluble particulate, whereby 5 to 90% of the water insoluble particulate is made from a water insoluble particulate material, having a weight mean particle size of less than 20 microns and an oil absorption capacity of 90 to 145 cm$^3$/100 g, and selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice, and 5 to 90% of the water insoluble particulate is made from an amorphous silica, having a weight mean particle size of below 20 microns and an oil absorption 150 to 190 cm$^3$/100 g.

5. Inorganic material in granular form according to claim 1, comprising at least 95% w/w of a water insoluble particulate, whereby 5 to 90% of the water insoluble particulate is made from a water insoluble particulate material, having a weight mean particle size of less than 20 microns and an oil absorption capacity of 90 to 145 cm$^3$/100 g, and selected from the group consisting of aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice, and 5 to 90% of the water insoluble particulate is made from an amorphous silica, having a weight mean particle size of below 20 microns and an oil absorption of 130 to 190 cm$^3$/100 g.

6. Inorganic material in granular form according to claim 4 having a particle size of 95% below 1000 microns and 95% above 45 microns, as measured by sieve analysis.

7. Inorganic material in granular form according to claim 5 having a particle size of 95% below 1000 microns and 95% above 45 microns, as measured by sieve analysis.

8. Cosmetic composition comprising 1 to 20% by weight of an inorganic material according to claim 1.

9. Cosmetic composition comprising an inorganic material in granular form, characterized in that the inorganic material in granular form, under condition of use of the cosmetic composition, breaks down to a particle size wherein less than 5% by weight is above 45 microns, as measured by wet sieve analysis.

10. Inorganic material according to claim 1 wherein less than 2% by weight of the residue remains on the 45 micron wet sieve.

11. Inorganic material according to claim 10 wherein less than 1% by weight of the residue remains on the 45 micron wet sieve.

12. Cosmetic composition according to claim 8 which comprises 1 to 10% by weight of the inorganic material.

13. Cosmetic composition according to claim 9 wherein less than 2% by weight of the particle size is above 45 microns.

14. Cosmetic composition according to claim 13 wherein less than 1% by weight of the particle size is above 45 microns.

15. Cosmetic composition for application to the skin, said composition comprising a particulate inorganic material which, in use of the composition by application to the skin, initially confers abrasivity but thereafter breaks down into smaller particles, wherein the inorganic material utilized in the cosmetic composition is one which is in granular form such that less than 5% by weight residue remains on a 45 micron wet sieve after ultrasonification for 7 minutes with 60 micron amplitude of vibration.

16. Cosmetic composition according to claim 15 wherein less than 2% by weight residue remains on the 45 micron wet sieve.

17. Cosmetic composition according to claim 16 wherein less than 1% by weight residue remains on the 45 micron wet sieve.

18. Cosmetic composition according to claim 15 which is in the form of a liquid, emulsion, cream, paste or gel.

19. Cosmetic composition according to claim 15 wherein the inorganic material comprises at least 95% by weight of amorphous silicas.

20. Cosmetic composition according to claim 19 wherein the inorganic material comprises at least 95% by weight of amorphous silica agglomerates.

21. Cosmetic composition according to claim 15 which comprises inorganic material in granular form, said inorganic material comprising at least 95% w/w of a water insoluble particulate, whereby 5 to 90% of the water insoluble particulate is made from a water insoluble particulate material, having a weight mean particle size of less than 20 microns and an oil absorption capacity of 90 to 145 cm$^3$/100 g, and selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice, and 5 to 90% of the water insoluble particulate is made from an amorphous silica, having a weight mean particle size of below 20 microns and an oil absorption of 150 to 190 cm$^3$/100 g.

22. Cosmetic composition according to claim 15 which comprises inorganic material in granular form, said inorganic material comprising at least 95% w/w of a water insoluble particulate, whereby 5 to 90% of the water insoluble particulate is made from a water insoluble particulate material, having a weight mean particle size of less than 20 microns and an oil absorption capacity of 90 to 145 cm$^3$/100 g, and selected from the group consisting of aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice, and 5 to 90% of the water insoluble particulate is made from an amorphous silica, having a weight mean particle size of below 20 microns and an oil absorption of 130 to 190 cm$^3$/100 g.

23. Cosmetic composition according to claim 21 which comprises inorganic material in granular form having a particle size of 95% below 1000 microns and 95% above 45 microns, as measured by sieve analysis.

24. Cosmetic composition according to claim 22 which comprises inorganic material in granular form having a particle size of 95% below 1000 microns and 95% above 45 microns, as measured by sieve analysis.

* * * * *